(12) United States Patent
Hoge

(10) Patent No.: US 7,112,797 B2
(45) Date of Patent: Sep. 26, 2006

(54) SCINTILLATOR HAVING INTEGRATED COLLIMATOR AND METHOD OF MANUFACTURING SAME

(75) Inventor: Michael F. Hoge, Waukesha, WI (US)

(73) Assignee: General Electric Company, Schenectady, NY (US)

(*) Notice: Subject to any disclaimer, the term of this patent is extended or adjusted under 35 U.S.C. 154(b) by 111 days.

(21) Appl. No.: 10/249,699

(22) Filed: Apr. 30, 2003

(65) Prior Publication Data

US 2004/0217291 A1 Nov. 4, 2004

(51) Int. Cl.
*G21K 1/02* (2006.01)
(52) U.S. Cl. .................. 250/363.1; 250/515.1
(58) Field of Classification Search .......... 250/363.1, 250/515.1
See application file for complete search history.

(56) References Cited

U.S. PATENT DOCUMENTS 4,982,096 A * 1/1991 Fujii et al. ................ 250/367
6,707,875 B1 * 3/2004 Fenkart et al. .............. 378/4
2004/0179645 A1 * 9/2004 Hoffman et al. ............ 378/19

FOREIGN PATENT DOCUMENTS

GB 2034148 A * 5/1980
JP 2004333490 A * 11/2004

* cited by examiner

*Primary Examiner*—Otilia Gabor
*Assistant Examiner*—Christine Sung
(74) *Attorney, Agent, or Firm*—Ziolkowski Patent Solutions Group, SC; Michael A. Della Penna; Carl B. Horton

(57) ABSTRACT

The present invention is directed to an integrated scintillator and collimator array for a CT detector. The integrated scintillator and collimator are fabricated from a manufacturing process or technique whereupon an array of scintillator material is positioned on a tooling base such that a collimator mold housing having a collimator mold therein may be positioned on the block of scintillator material. The block and mold housing are then aligned allowing a collimator mixture to be disposed into the mold. The collimator mixture is then allowed to cure to form an integrated scintillator and collimator.

31 Claims, 7 Drawing Sheets

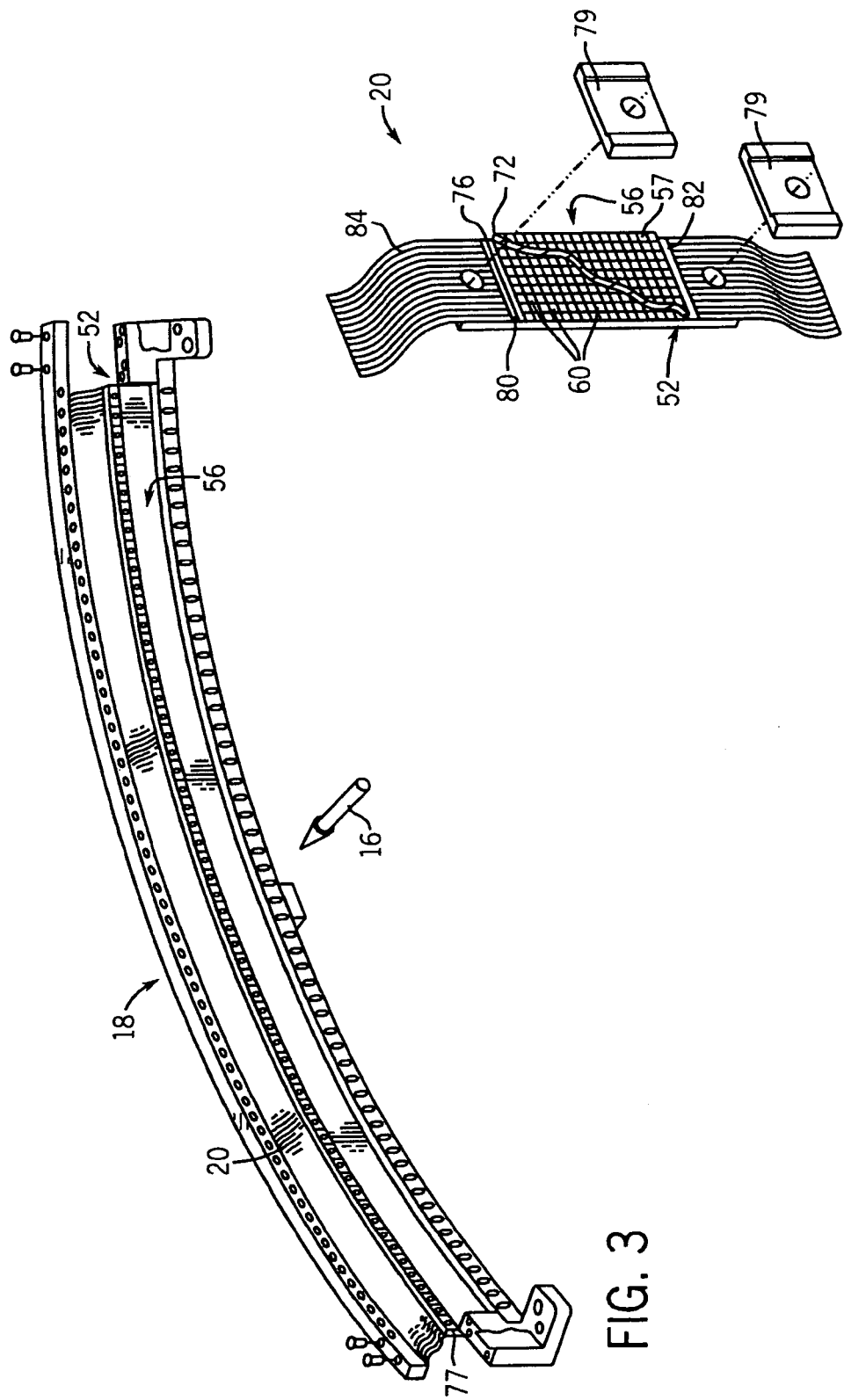

SCINTILLATOR HAVING INTEGRATED COLLIMATOR AND METHOD OF MANUFACTURING SAME

BACKGROUND OF INVENTION

The present invention relates generally to diagnostic imaging and, more particularly, to an integrated scintillator and collimator and method of manufacturing same.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

As stated above, typical x-ray detectors include a collimator for collimating x-ray beams such that collection of scattered x-rays is minimized. As such, the collimators operate to attenuate off-angle scattered x-rays from being detected by a scintillator cell. Reducing this scattering reduces noise in the signal and improves the final reconstructed image. Therefore, it is necessary that the scintillator array and the collimator, typically plates extending along one dimension above the scintillator array, are uniformly aligned. That is, exact mechanical alignment is required between the collimator plates and the cast reflector lines in the array of scintillators.

Known manufacturing processes attempt this exact alignment by constructing a continuous collimator that is sized to dimensionally match the width and length of the entire detector array. That is, the collimator plates are arranged or arrayed in a continuous consistent pattern or pitch that spans the entire detector length and is placed and attached to the detector rail structure. As such, individual scintillator arrays or packs are must then be exactly aligned to the continuous collimator to ensure that all scintillator cells and collimator cells are aligned exactly; otherwise the collimator must be discarded or repaired, or the scintillator packs must be discarded. This process requires excessively tight tolerancing and requires great operator skill and patience to assemble. Accordingly, these known processes are susceptible to waste of parts, material, and labor.

Additionally, as CT detectors grow in the z-direction, alignment requirements will tighten and the number of cells requiring alignment will increase. Therefore, the low process yields and high-end process scrap and re-work associated with these known manufacturing processes will increase the cost and time associated with CT detector assembly.

Notwithstanding the advances made in CT detector manufacturing, these known detector assemblies and assembly processes result in a detector with less than optimal collimation. Referring to FIG. 10, a known CT detector 1 fabricated according to known manufacturing processes is shown. The CT detector 1 includes a series of tungsten collimator plates 2 that collimate x-rays projected toward scintillator cells 3 of a scintillator array 4. As shown, each of the collimator plates 2 is generally aligned with a reflector line 5 disposed between adjacent scintillators 3. The reflector lines 5 prevent light from being emitted between adjacent scintillators. The scintillator array is coupled to a photodiode array 6 that detects light emissions from the scintillator array and transmits corresponding electrical signals to a data acquisition system for signal processing. As readily shown, the collimator plates are not integrated with the individual scintillator elements 3. That is, an air gap 7 exists between the collimator plates and the scintillator cells 3. The air gap 7 typically results in a separation between the collimator plates and the scintillator array of approximately two to four thousands of an inch. This air gap occurs as a result of the manufacturing process whereupon the collimator plates are formed as a single collimator assembly that accepts and aligns an array of scintillators. The air gap, however, makes the CT detector susceptible to x-rays received between two collimator plates impinging upon an adjacent scintillator thereby resulting in undesirable anomalies in the final reconstructed CT image.

Therefore, it would be desirable to design an integrated scintillator and collimator absent the aforementioned air gap as well as a method of manufacturing such an integrated scintillator and collimator.

BRIEF DESCRIPTION OF INVENTION

The present invention is directed to an integrated scintillator and collimator and method of manufacturing same that overcome the aforementioned drawbacks. The integrated scintillator and collimator reduces x-ray cross-talk between adjacent detector cells and improves dimensional alignment between collimator septum and scintillator reflector walls by integrating collimator plates with a top reflector surface of a scintillator. A pixilated array of scintillators is placed on a tooling base whereupon a mold having a series of parallel aligned air cavities is positioned atop the array of scintillators. The air cavities within the mold are positioned such that each aligns with a reflector line in the scintillator array. Using high precision tooling, the mold and the scintillator array are precisely aligned relative to one another. Upon proper alignment, a vacuum pump is used to remove the air cavities from within the mold. Thereafter, an injector is used to dispose collimator mixture within the mold and which is allowed to cure. Once the collimator mixture has cured, the integrated scintillator/collimator is formed.

Therefore, in accordance with one aspect of the present invention, a method of manufacturing a detector having an integrated scintillator and collimator is provided. The method includes the steps of positioning an array of scintillator elements or pack on a tooling base and positioning a collimator mold housing having a collimator mold cavity therein on the block. As a result, the mold cavity will be very accurately aligned to the scintillator array pattern. A collimator mixture is then disposed into the mold cavity and allowed to cure to form an integrated scintillator and collimator.

In accordance with another aspect of the present invention, a detector for a CT system includes an array of scintillation elements arranged to convert received x-rays to light. A plurality of collimator elements is integrally formed in a top surface of the array of scintillation elements and operates to attenuate off-angle scattered x-rays from being detected by scintillator elements. The detector further includes an array of photodiode elements arranged to receive light emissions from the array of scintillation elements.

According to another aspect of the present invention, an integrated scintillator and collimator array is formed by the steps of placing an array of pixilated scintillators on a tooling base and positioning a collimator mold defining a plurality of cavities that extend to a top surface of the array adjacent the array. A collimator material is then disposed within the plurality of cavities and cured so as to form the integrated scintillator and collimator array.

In accordance with yet another aspect of the present invention, an apparatus for manufacturing an integrated scintillator and collimator includes a tooling base designed to support a block of scintillating material and a mold to be positioned on the block of scintillating material. An alignment mechanism is provided to align the block in the mold in an aligned arrangement as well as a mold evacuator designed to remove air cavities within the mold. A collimator mixture supply is also provided to supply collimator material to the mold.

According to yet another aspect of the present invention, a system to manufacture an integrated scintillator/collimator includes means for positioning a block of scintillator pack on a tooling base as well as means for positioning a collimator mold over the block. Means for aligning the block and the collimator mold is provided as well as means for removing air cavities from the mold. The system also includes means for disposing collimator material into a volume previously occupied by the removed air cavities and means for curing the collimator material to form an integrated scintillator and collimator.

Various other features, objects and advantages of the present invention will be made apparent from the following detailed description and the drawings.

BRIEF DESCRIPTION OF DRAWINGS

The drawings illustrate one preferred embodiment presently contemplated for carrying out the invention.

In the drawings:

FIG. 3 is a perspective view of one embodiment of a CT system detector array.

FIG. 4 is a perspective view of one embodiment of a detector.

FIG. 10 is a cross-sectional schematic diagram of a known detector.

DETAILED DESCRIPTION

The operating environment of the present invention is described with respect to a four-slice computed tomography (CT) system. However, it will be appreciated by those skilled in the art that the present invention is equally applicable for use with single-slice or other multi-slice configurations. Moreover, the present invention will be described with respect to the detection and conversion of x-rays. However, one skilled in the art will further appreciate that the present invention is equally applicable for the detection and conversion of other high frequency electromagnetic energy. The present invention will be described with respect to a "third generation" CT scanner, but is equally applicable with other CT systems.

Figure 1:
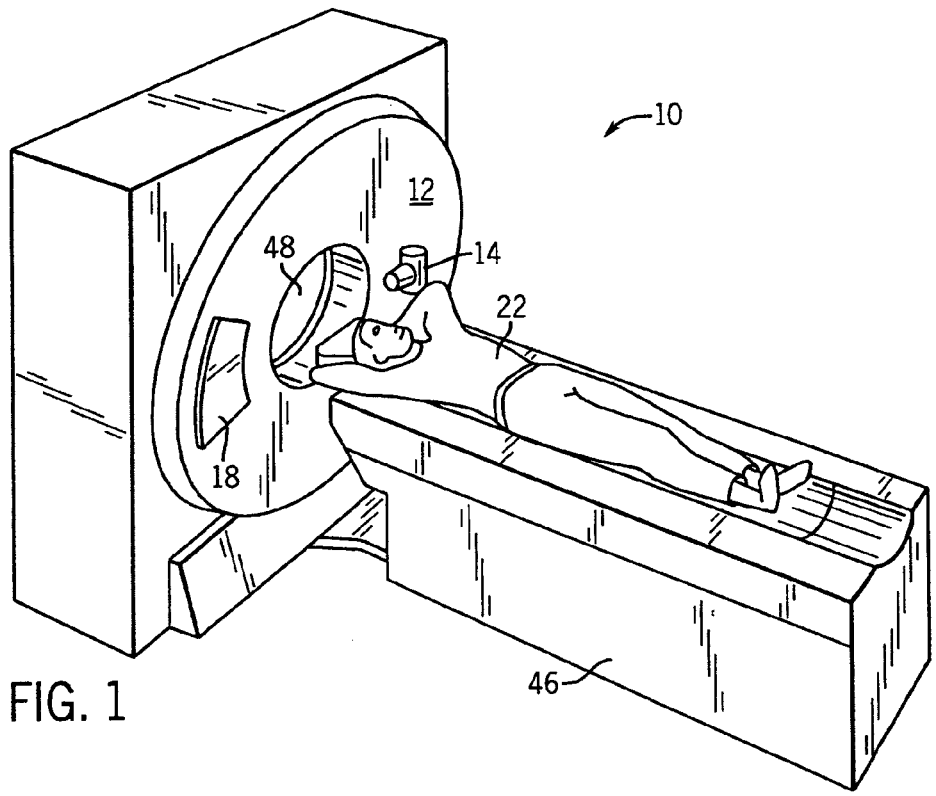
FIG. 1 is a pictorial view of a CT imaging system.
Figure 2:
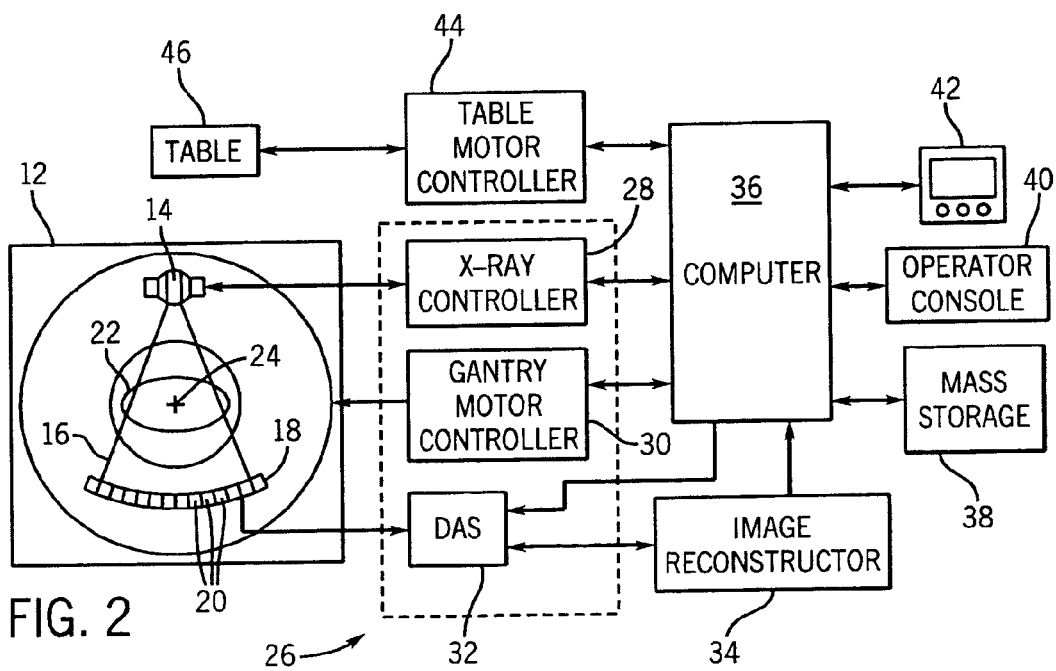
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

As shown in FIGS. 3 and 4, detector array 18 includes a plurality of scintillators 57 forming a scintillator array 56. A collimator (not shown) is positioned above scintillator array 56 to collimate x-ray beams 16 before such beams impinge upon scintillator array 56.

In one embodiment, shown in FIG. 3, detector array 18 includes 57 detectors 20, each detector 20 having an array size of 16×16. As a result, array 18 has 16 rows and 912 columns (16×57 detectors) which allows 16 simultaneous slices of data to be collected with each rotation of gantry 12.

Switch arrays 80 and 82, FIG. 4, are multi-dimensional semiconductor arrays coupled between scintillator array 56 and DAS 32. Switch arrays 80 and 82 include a plurality of field effect transistors (FET) (not shown) arranged as multi-dimensional array. The FET array includes a number of electrical leads connected to each of the respective photodiodes 60 and a number of output leads electrically connected to DAS 32 via a flexible electrical interface 84. Particularly, about one-half of photodiode outputs are electrically connected to switch 80 with the other one-half of photodiode outputs electrically connected to switch 82. Additionally, a reflector layer (not shown) may be interposed between each scintillator 57 to reduce light scattering from adjacent scintillators. Each detector 20 is secured to a detector frame 77, FIG. 3, by mounting brackets 79.

Switch arrays 80 and 82 further include a decoder (not shown) that enables, disables, or combines photodiode outputs in accordance with a desired number of slices and slice resolutions for each slice. Decoder, in one embodiment, is a decoder chip or a FET controller as known in the art. Decoder includes a plurality of output and control lines coupled to switch arrays 80 and 82 and DAS 32. In one embodiment defined as a 16 slice mode, decoder enables switch arrays 80 and 82 so that all rows of the photodiode array 52 are activated, resulting in 16 simultaneous slices of data for processing by DAS 32. Of course, many other slice combinations are possible. For example, decoder may also select from other slice modes, including one, two, and four-slice modes.

Figure 5:
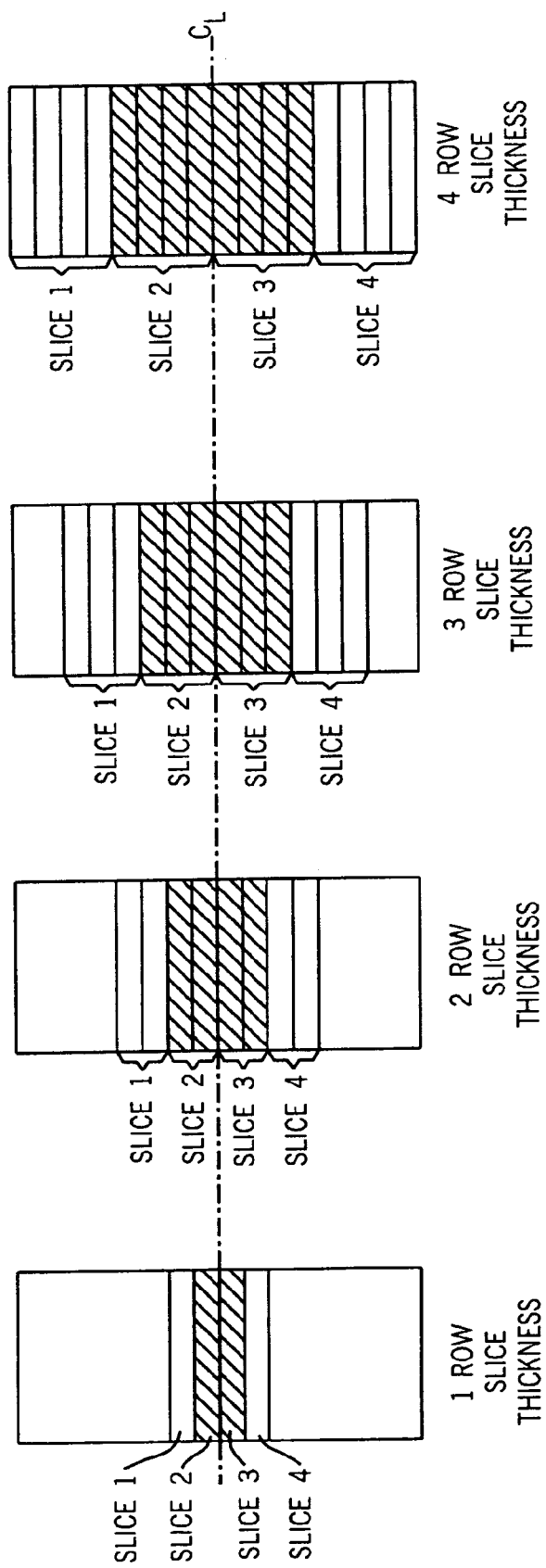
FIG. 5 is illustrative of various configurations of the detector in FIG. 4 in a four-slice mode.

As shown in FIG. 5, by transmitting the appropriate decoder instructions, switch arrays 80 and 82 can be configured in the four-slice mode so that the data is collected from four slices of one or more rows of photodiode array 52. Depending upon the specific configuration of switch arrays 80 and 82, various combinations of photodiodes 60 can be enabled, disabled, or combined so that the slice thickness may consist of one, two, three, or four rows of scintillator array elements 57. Additional examples include, a single slice mode including one slice with slices ranging from 1.25 mm thick to 20 mm thick, and a two slice mode including two slices with slices ranging from 1.25 mm thick to 10 mm thick. Additional modes beyond those described are contemplated.

Figure 6:
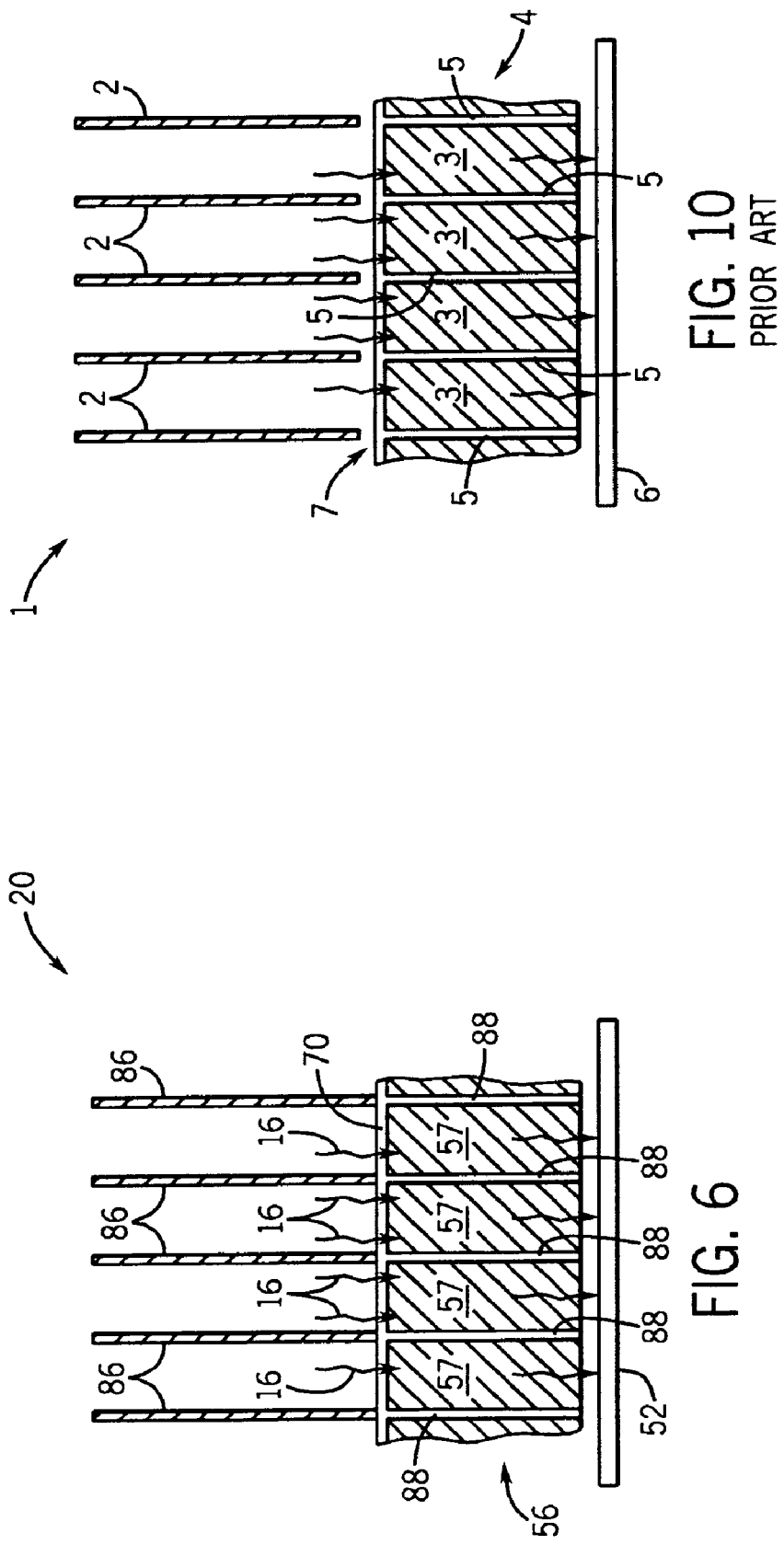
FIG. 6 is a cross-sectional schematic diagram of a detector in accordance with the present invention.

Referring now to FIG. 6, a CT detector having an integrated scintillator and collimator is schematically shown. The detector 20 includes a photodiode array 52 coupled to receive light emissions from a scintillator array 56 of scintillation elements 57. Cast directly onto the scintillation array or pack is a plurality of collimator plates 86. The collimator plates 86 are precisionally aligned with reflector lines 88 disposed between the scintillator elements 57. By casting the collimator plates directly onto the scintillator pack, the air gap discussed with reference to FIG. 10 is eliminated thereby improving the collimation achieved by collimator plates 86. As will be described in greater detail below, each of the collimator plates is formed by a combination or mixture of tungsten and epoxy.

Casting the collimator plates directly onto a top reflective surface 90 of the scintillator pack improves the rigidity of the scintillator/collimator structure thereby improving the detector's response to loads induced by a rotating gantry during CT data acquisition. That is, the collimator plates of a CT detector 1 similar to that shown in FIG. 10 are susceptible to gravitational and rotational forces induced movement as a result of the collimator plates being separated from the scintillator array by the previously discussed air gap. The CT detector illustrated in FIG. 6, however, has reduced susceptibility to the aforementioned gravitational forces as a result of the collimator plates being directly cast onto the scintillator pack.

Figure 7:
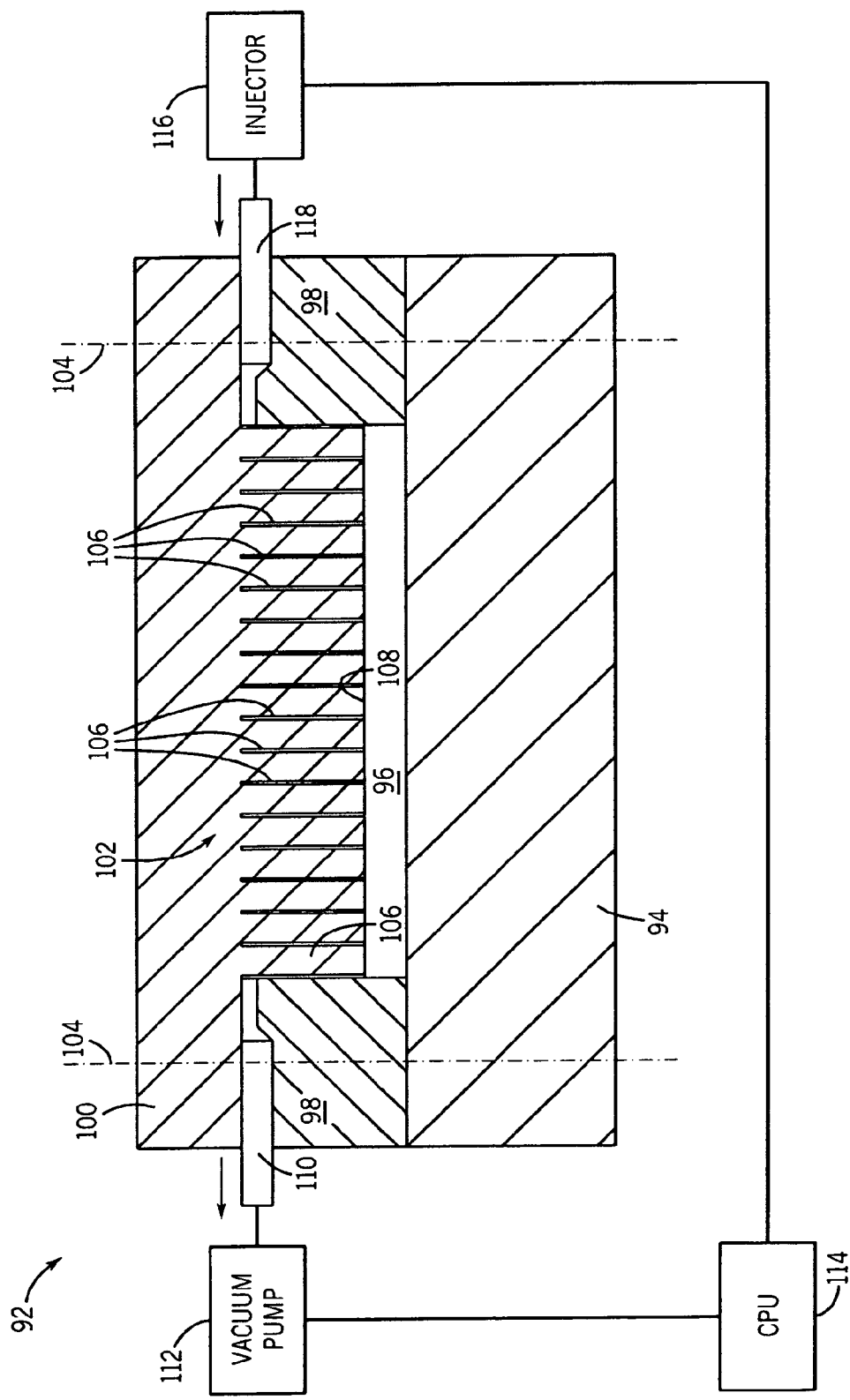
FIG. 7 is a cross-sectional schematic diagram of an assembly to manufacture an integrated scintillator and collimator in accordance with the present invention.

Referring now to FIG. 7, a tooling assembly 92 for manufacturing an array of integrated scintillators and collimators is shown. The tooling assembly includes a tooling base 94 designed to support a scintillator array cast pack 96 that is positioned within the lower mold cavity 98. The lower mold cavity 98 is aligned with an upper mold housing 100 such that the pack 96 and mold 102 are properly aligned with respect to one another. To ensure proper and precisioned alignment, tooling assembly 92 includes a dowel pin alignment assembly 104. Other dowel pins and alignment tools such as bore datums (not shown) are contemplated and applicable with the illustrated assembly.

In the illustrated embodiment, mold 102 includes a series of cavities 106 that is uniformly aligned in parallel relative to cast pack 96. Further, each cavity 106 has a height equal to the desired height of a collimator plate and extends to the top surface 108 of scintillator array cast pack 96.

Assembly 92 further includes an evacuation gate 110 that is connected to a vacuum pump 112. The vacuum pump is controlled by a CPU 114 to remove air from each cavity 106. When the mold is positioned atop the scintillator pack, air fills cavities 106. This air must be removed for proper formation of the collimator, as will be described hereinafter. As such, pump 112 is used to remove air from cavities 106. After a vacuum is formed within the mold housing 100, a collimator mixture is injected by injector 116 through fill gate 118 such that each of the cavities 106 is filled with collimator mixture. The collimator mixture may directly injected by injector 116 or drawn into the mold cavity by the vacuum created in the cavity upon removal of air from within the cavity. The collimator mixture is preferably a combination of tungsten and epoxy. Additionally, the collimation is preferably a powder. However, other combinations, mixtures, and combinations and in non-powder forms may be equivalently used. The collimator mixture is cured at room temperature or elevated temperatures within the mold housing 100. Once cured, the mold housing is removed thereby leaving a series of collimator plates integrally formed with a top surface of the scintillator pack.

Figure 8:
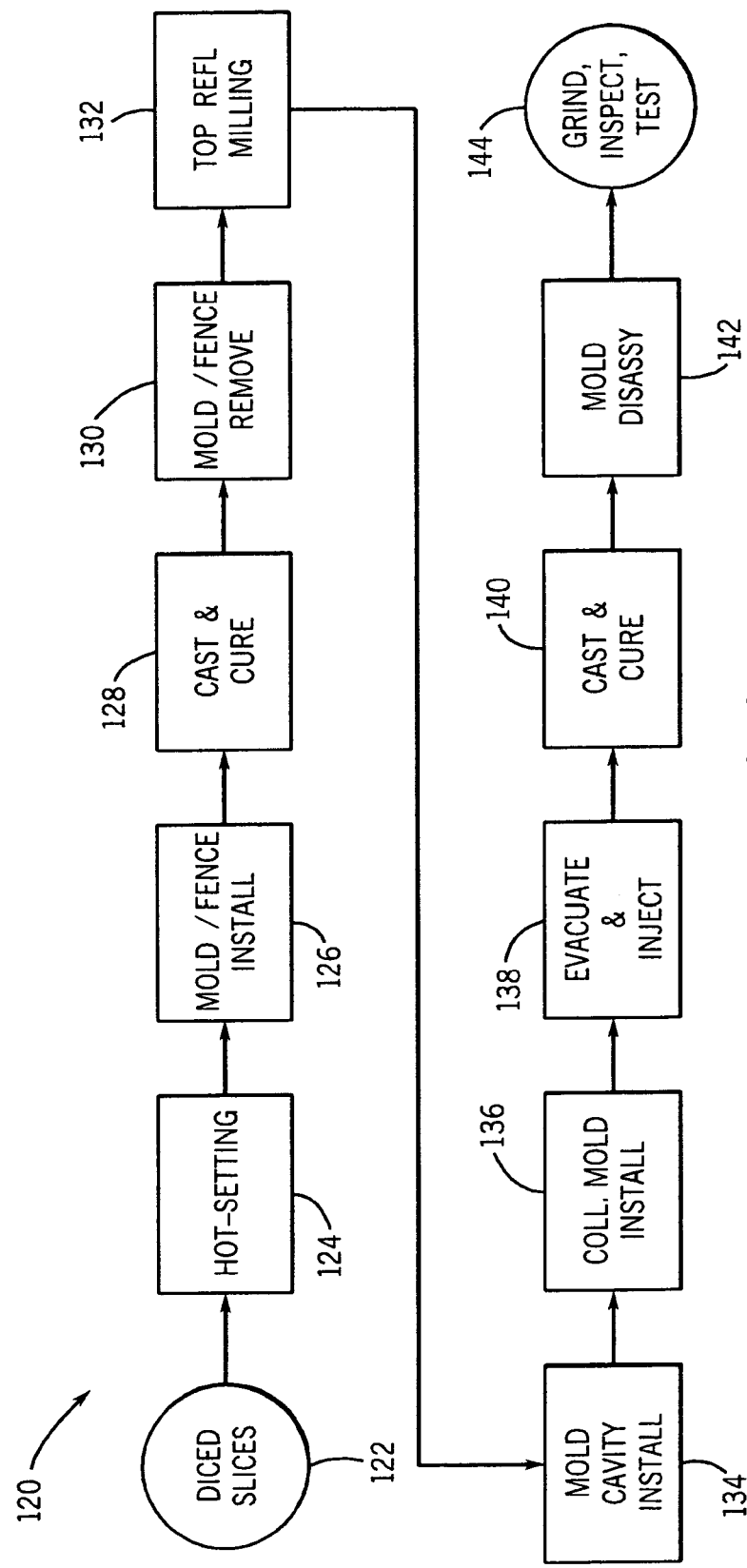
FIG. 8 is a pictorial view of a CT system for use with a non-invasive package inspection system.

Referring now to FIG. 8, a manufacturing process 120 for manufacturing an integrated scintillator and collimator array begins at 122 with a series of diced slices of scintillator material undergoing a hot setting process at 124. After undergoing the hot setting process 124, a mold or fence is installed at 126. The mold is used to properly dispose reflector material between each scintillation element. The material used to form the reflector layer is allowed to cast and cure 128 whereupon the mold is removed at 130. The resulting scintillator array cast pack having the reflector lines integrated therewith is milled at 132.

Following milling of the top reflective layer of the cast pack, a collimator cavity is positioned about the milled scintillator pack at 134. As stated above, the mold cavity is used during aligning of the scintillator pack relative to the collimator mold. Once the mold cavity and scintillator pack are properly positioned on a tooling base, a collimator mold is positioned or installed relative to the scintillator pack and mold cavity at 136. The collimator mold cavity and scintillator pack are properly aligned using a dowel pin alignment assembly and a series of bore datums, as was previously described. Once the mold, cavity, and block are properly aligned, the air contained in each of the cavities, as a result of the positioning of the mold on the scintillator pack, is removed using a vacuum pump. Once a vacuum is created within the mold, the collimator mixture or powder is introduced into each of the cavities 138. The injected mixture is then allowed to cure 140 thereby resulting in a series of collimator plates being formed integrally with a top surface of the scintillator pack. The mold assembly is then disassembled at 142 resulting in an array of integrated scintillators and collimators. The resulting assembly then undergoes a grinding, inspection, and testing stage 144 to ensure proper alignment and fabrication of the integrated scintillator and collimator array 144.

The present invention has been described with respect to fabrication of integrated scintillator and collimator for a CT detector of a CT imaging system. CT detectors incorporating an integrated scintillator and collimator in accordance with the present invention may be used in medical imaging systems as well as parcel inspections systems similar to those illustrated in FIG. 9.

Figure 9:
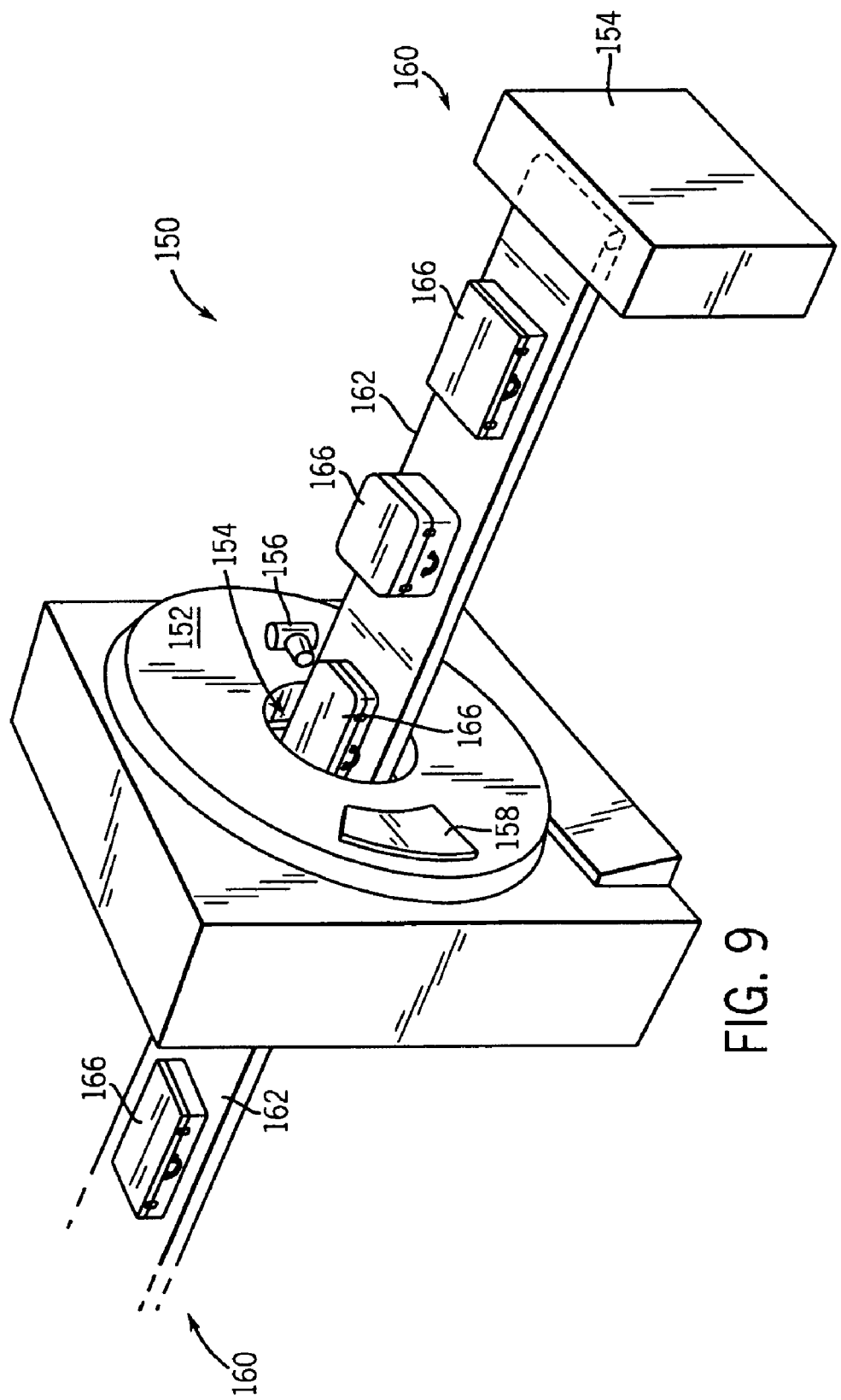
FIG. 9 is a flow chart setting forth the steps of a manufacturing process or technique for forming an integrated scintillator/collimator in accordance with the present invention.

Referring to FIG. 9, package/baggage inspection system 150 includes a rotatable gantry 152 having an opening 154 therein through which packages or pieces of baggage may pass. The rotatable gantry 152 houses a high frequency electromagnetic energy source 156 as well as a detector assembly 158 having arrays of integrated scintillator/collimator cells similar to that shown in FIG. 6 and fabricated using an assembly apparatus similar to that described with respect to FIG. 7. A conveyor system 160 is also provided and includes a conveyor belt 162 supported by structure 164 to automatically and continuously pass packages or baggage pieces 166 through opening 154 to be scanned. Objects 166 are fed through opening 154 by conveyor belt 162, imaging data is then acquired, and the conveyor belt 162 removes the packages 166 from opening 164 in a controlled and continuous manner. As a result, postal inspectors, baggage handlers, and other security personnel may non-invasively inspect the contents of packages 166 for explosives, knives, guns, contraband, etc.

The present invention has been described with respect to fabricating an integrated scintillator and collimator for a CT based imaging system. Further, fabrication of a rectangular shaped scintillator/collimator combination has been described. However, the present invention contemplates additional patterns or shaped cells being fabricated. Additionally, the present invention envisions numerous collimator material combinations beyond the tungsten/epoxy mixture previously described. Additionally, the high precision alignment and tooling aspects of the present invention may be used to support different "molding" processes such as extrusion, injection molding, and the like. The high precision alignment and tooling aspects could be also applied to electronics packaging application to provide x-ray shielding of sensitive components.

Additionally, the present invention has been described with respect to an integrated scintillator whereupon the collimator plates are cast along one dimensional, i.e., the z-axis. However, integrated scintillators and collimators may be formed using the aforementioned methods of manufacturing along an x and z axis thereby rendering a "checkerboard" full two-dimensional (2D) arrangement of integrated scintillators and collimators. The present invention may be implemented to create a partial 2D array of integrated scintillator and collimators. That is, the collimator mold may be constructed such that the collimator cavities have different heights when filled with the collimator mixture. As a result, the collimator plates along one axis, i.e., the z-axis, may have a greater height than collimator plates along another axis, i.e., the x-axis.

Therefore, in accordance with one embodiment of the present invention, a method of manufacturing a detector having an integrated scintillator and collimator is provided. The method includes the steps of positioning an array of scintillator elements or pack on a tooling base and positioning a collimator mold housing having a collimator mold cavity therein on the block. As a result, the mold cavity will be very accurately aligned to the scintillator array pattern. A collimator mixture is then disposed into the mold cavity and allowed to cure to form an integrated scintillator and collimator.

In accordance with another embodiment of the present invention, a detector for a CT system includes an array of scintillation elements arranged to convert received x-rays to light. A plurality of collimator elements is integrally formed in a top surface of the array of scintillation elements and operates to attenuate off-angle scattered x-rays from being detected by scintillator elements. The detector further includes an array of photodiode elements arranged to receive light emissions from the array of scintillation elements.

According to another embodiment of the present invention, an integrated scintillator and collimator array is formed by the steps of placing an array of pixilated scintillators on a tooling base and positioning a collimator mold defining a plurality of cavities that extend to a top surface of the array adjacent the array. A collimator material is then disposed within the plurality of cavities and cured so as to form the integrated scintillator and collimator array.

In accordance with yet another embodiment of the present invention, an apparatus for manufacturing an integrated scintillator and collimator includes a tooling base designed to support a block of scintillating material and a mold to be positioned on the block of scintillating material. An alignment mechanism is provided to align the block in the mold in an aligned arrangement as well as a mold evacuator designed to remove air cavities within the mold. A collimator mixture supply is also provided to supply collimator material to the mold.

According to yet another embodiment of the present invention, a system to manufacture an integrated scintillator/collimator includes means for positioning a block of scintillator pack on a tooling base as well as means for positioning a collimator mold over the block. Means for aligning the block and the collimator mold is provided as well as means for removing air cavities from the mold. The system also includes means for disposing collimator material into a volume previously occupied by the removed air cavities and means for curing the collimator material to form an integrated scintillator and collimator.

The present invention has been described in terms of the preferred embodiment, and it is recognized that equivalents, alternatives, and modifications, aside from those expressly stated, are possible and within the scope of the appending claims.

What is claimed is:

1. A method of manufacturing a detector having an integrated scintillator and collimator, the method comprising the steps of:

positioning a block of scintillator pack on a tooling base;
    positioning a collimator mold housing having a collimator mold cavity therein on the block;
    aligning the block and the mold housing;
    disposing a collimator mixture into the mold cavity; and
    curing the collimator mixture to form an integrated scintillator and collimator.

2. The method of claim 1 further comprising the step of milling a top reflector surface of the block prior to positioning the collimator mold over the block.

3. The method of claim 1 further comprising the step of fastening the block and the collimator mold housing together after the aligning.

4. The method of claim 1 wherein the step of aligning includes the step of properly orienting the block, the collimator mold housing, and the mold cavity relative to one another with a set of pins.

5. The method of claim 1 wherein the collimator mold cavity includes a series of parallel-aligned cavities designed to receive the collimator mixture.

6. The method of claim 1 wherein the collimator mold housing is formed of stainless steel.

7. The method of claim 1 further comprising the step of removing air from the mold cavity using a vacuum pump.

8. The method of claim 1 wherein the collimator mixture includes a combination of tungsten and epoxy.

9. The method of claim 1 further comprising the step of grinding the integrated scintillator and collimator.

10. A detector comprising:
   an array of scintillation elements arranged to convert received x-rays to light;
   a plurality of collimator elements molded to an x-ray's reception surface of the array of scintillation elements to collimate x-ray's toward individual scintillation elements; and
   an array of photodiode elements arranged to receive light emissions from the array of scintillation elements.

11. The detector of claim 10 wherein each of the plurality of collimator elements is fabricated from a tungsten/epoxy combination.

12. The detector of claim 10 wherein the plurality of collimator elements is arranged along more than one dimension.

13. The detector of claim 10 wherein the plurality of collimator elements is two-dimensionally arranged.

14. The detector of claim 10 further comprising a pair of FET arrays connected to the plurality of photodiode elements to transmit signal output by the plurality of photodiode elements to a data acquisition system.

15. The detector of claim 10 incorporated into a CT imaging system.

16. The detector of claim 15 wherein the CT imaging system includes at least a medical scanner and a parcel inspection apparatus.

17. An integrated scintillator and collimator array formed by the steps of:
   placing an array of pixilated scintillators on a tooling base;
   positioning a collimator mold defining a plurality of cavities that extend adjacent to a top surface of the array;
   disposing a combination of collimator material within the plurality of cavities; and
   curing the collimator material.

18. The array of claim 17 further comprising the step of positioning the array and the plurality of cavities such that the array and cavities are uniformly aligned with respect to one another.

19. The array of claim 18 wherein the step of aligning further includes the step of orienting the any of pixilated scintillators and the collimator mold with respect to a set of pins and bore datums.

20. The array of claim 18 further comprising the step of removing air from the plurality of cavities by vacuum pumping the air through an evacuation gate.

21. The array of claim 18 wherein the collimator material includes tungsten and epoxy.

22. The array of claim 18 wherein the tungsten has a powder form.

23. An apparatus for manufacturing an integrated scintillator and collimator, the apparatus comprising:
   a tooling base designed to support a block of scintillating material;
   a mold to be positioned on the block of scintillating material;
   an alignment mechanism to align the block and the mold in an aligned arrangement; and
   a collimator mixture supply to supply collimator material to the mold.

24. The apparatus of claim 23 wherein the alignment mechanism includes a set of pins and bore datums and the collimator mixture supply includes an injector to inject collimator material within the mold.

25. The apparatus of claim 23 wherein the collimator mixture supply is configured to supply tungsten and epoxy to the cavities.

26. The apparatus of claim 25 wherein the tungsten and epoxy are a powder.

27. The apparatus of claim 23 wherein the mold is formed of stainless steel.

28. The apparatus of claim 23 further comprising a computer to control manufacturing of the integrated scintillator and collimator.

29. The apparatus of claim 23 further comprising a mold evacuator designed to remove air from cavities in the mold.

30. The apparatus of claim 29 wherein the mold evacuator includes a vacuum pump.

31. A system to manufacture an integrated scintillator and collimator, the system comprising:
   means for positioning a block of scintillator pack on a tooling base;
   means for positioning a collimator mold over the block;
   means for aligning the block and the collimator mold;
   means for disposing a collimator material into the collimator mold; and
   means for curing the collimator material to form an integrated scintillator and collimator.

* * * * *

UNITED STATES PATENT AND TRADEMARK OFFICE
CERTIFICATE OF CORRECTION

| | |
|---|---|
| PATENT NO. | : 7,112,797 B2 |
| APPLICATION NO. | : 10/249699 |
| DATED | : September 26, 2006 |
| INVENTOR(S) | : Michael F. Hoge |

Page 1 of 1

It is certified that error appears in the above-identified patent and that said Letters Patent is hereby corrected as shown below:

Col. 9, line 21 (Claim 10), delete "x-ray's" and substitute therefore -- x-rays --;

Col. 10, line 2 (Claim 19), delete "any" and substitute therefore -- array --.

Signed and Sealed this

Twelfth Day of December, 2006

JON W. DUDAS
*Director of the United States Patent and Trademark Office*

UNITED STATES PATENT AND TRADEMARK OFFICE
CERTIFICATE OF CORRECTION

PATENT NO. : 7,112,797 B2 Page 1 of 1
APPLICATION NO. : 10/249699
DATED : September 26, 2006
INVENTOR(S) : Hoge et al.

It is certified that error appears in the above-identified patent and that said Letters Patent is hereby corrected as shown below:

On Title Page,

Item [*] Notice: Subject to any disclaimer, the term of this patent is extended or adjusted under 35 USC 154(b) by (0) days Delete the phrase "by 111 days" and insert -- by 412 days--

Signed and Sealed this

Twentieth Day of February, 2007

JON W. DUDAS
*Director of the United States Patent and Trademark Office*